United States Patent [19]

Leupold et al.

[11] Patent Number: 4,590,217

[45] Date of Patent: May 20, 1986

[54] PROCESS FOR THE MANUFACTURE OF ACETIC ACID, ACETALDEHYDE AND ETHANOL

[75] Inventors: Ernst I. Leupold, Neu-Anspach; Hans-Joachim Schmidt, Königstein; Friedrich Wunder, Flörsheim am Main, all of Fed. Rep. of Germany

[73] Assignee: Hoechst Aktiengesellschaft, Frankfurt, Fed. Rep. of Germany

[21] Appl. No.: 668,695

[22] Filed: Nov. 6, 1984

Related U.S. Application Data

[63] Continuation of Ser. No. 462,053, Jan. 28, 1983, abandoned.

[30] Foreign Application Priority Data

Jan. 30, 1982 [DE] Fed. Rep. of Germany ....... 3203060

[51] Int. Cl.$^4$ .............................................. C07C 27/06
[52] U.S. Cl. .................................... 518/716; 502/226; 502/230
[58] Field of Search ......................................... 518/716

[56] References Cited

U.S. PATENT DOCUMENTS 3,878,290  4/1975  Walkes .
4,224,236  9/1980  Wunder et al. .
4,351,908  4/1982  Schmidt et al. .

FOREIGN PATENT DOCUMENTS 1147749   6/1983  Canada .
0010295   4/1980  European Pat. Off. ............ 518/716
  22358   1/1981  European Pat. Off. .
57-130934 8/1982  Japan ................................. 518/716

OTHER PUBLICATIONS

Chem. Abstr., 97, 144362v (1982).
Chem. Abstr., 97, 16237g (1982).

*Primary Examiner*—Howard T. Mars
*Attorney, Agent, or Firm*—Curtis, Morris & Safford

[57] ABSTRACT

A method for making a mixture containing acetic acid, acetaldehyde, and ethanol as the pricipal products, which process comprises reacting carbon monoxide and hydrogen at an elevated temperature and at an elevated pressure in the presence of a supported catalyst prepared by impregnating a carrier with a salt or complex of rhodium and, as a promotor, with at least one non-oxidic compound of an element having an atomic number of 21, 39, or 58 to 71.

8 Claims, No Drawings

PROCESS FOR THE MANUFACTURE OF ACETIC ACID, ACETALDEHYDE AND ETHANOL

This is a continuation of application Ser. No. 462,053, filed Jan. 28, 1983, now abandoned.

The present invention provides a process for the manufacture of acetic acid, acetaldehyde and ethanol by reaction of carbon monoxide and hydrogen at elevated temperature and elevated pressure, in the presence of carrier catalysts containing rhodium and promoters.

It is known that the above compounds can be manufactured from carbon monoxide and hydrogen in the presence of carrier catalysts containing rhodium (German Auslegeschrift No. 2,503,233). By adding defined promoters or cocatalysts, the activity and/or selectivity of the latter to the above oxygen-containing compounds can be influenced. Such promoters are for example magnesium (German Offenlegungsschriften Nos. 2,712,732 and 2,814,265), manganese (German Auslegeschrift No. 2,628,463), iron (German Auslegeschrift No. 2,503,204) or one or more elements selected from the group consisting of zirconium, hafnium, lanthanium, chromium and mercury (German Offenlegungsschrift No. 2,846,148).

In the Published European Patent Application No. 22,358, rhodium catalysts are described which contain an oxide of a metal of groups IIa, IIIa, IVa or Va of the Periodic Table as cocatalyst, for example oxides of rare earths such as ceric oxide, neodymium oxide or yttrium oxide. However, the activity of these catalysts is poor, and they are not recommended for an economic manufacture of acetic acid, acetaldehyde and ethanol. Thus, generally less than 30 mol % of the carbon monoxide react to give ethanol, the remainder being converted mainly to methanol and hydrocarbons. Acetic acid and acetaldehyde are not formed in the presense of the cited catalysts or to an insignificant extent only.

Surprisingly, it has now been found that the activity and/or selectivity of the rhodium catalysts can be improved when they contain nonoxidic compounds of elements of the atomic numbers 21, 39 and 58 to 71.

The subject of the invention is therefore a process for the manufacture of acetic acid, acetaldehyde and ethanol by reaction of carbon monoxide and hydrogen at elevated temperature and elevated pressure in the presence of carrier catalysts containing rhodium and promoters, which comprises using as promoters one or more elements of the atomic numbers 21, 39 and 58 to 71 in the form of nonoxidic compounds.

In the process of the invention, carbon monoxide and hydrogen are reacted with high selectivity to acetic acid, acetaldehyde and ethanol. Additionally, small amounts of those products are obtained which are formed in a secondary reaction, for example by esterification, acetalization or condensation, that is, particularly ethyl acetate and the diethyl acetal of acetaldehyde. The amount of other oxygen-containing compounds having three or more carbon atoms in the molecule is very small and generally below 5 mol %, relative to reacted carbon monoxide. The total selectivity to oxygen-containing $C_2$ compounds including the products converted to ethyl acetate and acetaldehyde-diethylacetal is up to 82%, relative to reacted carbon monoxide. The remainder of the reacted carbon monoxide is converted substantially to methane and other gaseous hydrocarbons, and to a small extent to carbon dioxide.

Starting substances for the catalyst according to the invention may be salts or complex compounds of rhodium. Suitable are for example chlorides, bromides and iodides of rhodium or double salts of rhodium with alkali metal halides, such as dipotassium trichlororhodate. Further, complex compounds which in addition to rhodium and halogen contain complex-forming ligands, such as trialkylphosphines, triarylphosphines, carbon monoxide, olefins or water, that is, for example, tris-triphenylphosphine-rhodium-I-chloride, -bromide or -iodide, tristriphenylphosphine-rhodium-III-chloride, bis-tri-o-tolylphosphine-rodium-II chloride, carbonyl-bis-triphenylphosphine-rhodium-I bromide, or dicesium-carbonyl-pentachlororhodate-III are suitable. Those compounds of rhodium in which it is linked by a ionic or complex bond to a carrier, for example zeolites and ion exchangers exchanged with rhodium halides are also suitable.

As promoters according to the invention, there are used one or more elements of the atomic numbers 21, 39 and 58 to 71 in the form of nonoxidic compounds, for example the chlorides, bromides, fluorides, nitrates, acetates, acetylacetonates or tartrates, of scandium, yttrium, cerium, praseodymium, neodymium, promethium, samarium, europium, gadolinium, terbium, dysprosium, holmium, erbium, thulium, ytterbium and lutetium, preferably the chlorides, bromides, acetates and acetylacetonates of these elements. Particularly preferred are the chlorides, bromides, acetates and acetylacetonates of yttrium, gadolinium, dysprosium, holmium and ytterbium, especially the chlorides of these elements.

In addition to the above promoters, the rhodium catalysts may contain further cocatalytically active compounds, for example compounds of magnesium, lanthanum, manganese, tungsten, iron, furthermore halides or alkali metal salts. By addition of these compounds, the efficiency and/or selectivity of the catalysts may be improved further.

As catalysts carrier, conventional carrier materials having different specific surfaces are used. However, carriers having a specific surface of from 50 to 1,000 $m^2/g$ are preferred. For example, silicic acid and natural and synthetic silicates of elements of the IInd to VIIIth group of the Periodic Table (that is, for example, the silicates of magnesium, calcium, aluminium, manganese) are suitable, furthermore aluminum oxide, thorium dioxide, zeolites or spinels. Preferably, silicic acid or silicates are used. For preparing the catalysts, the rhodium compound, the promoters according to the invention and optionally further additives influencing the activity and/or selectivity of the catalysts are applied to the carrier either simultaneously or in subsequent steps in any sequence, generally by impregnation of the carrier with solutions of the active components in suitable solvents such as water, alcohol, acetone, acetylacetone or acetic acid, followed by drying.

Preferably, the catalyst is reduced before the start of the synthesis gas reaction. Suitable reducing agents are, for example, hydrogen, carbon monoxide, methanol or acetone. The reduction can be carried out in a separate apparatus or in the reactor, preferably at a temperature below 300° C., especially from 100° to 275° C. It is often advantageous to use for the reduction not the undiluted reducing gases alone but with addition of a certain amount of inert gases such as nitrogen, carbon dioxide or noble gases.

The concentration of rhodium and promoter(s) in the catalysts may be varied within wide limits; generally, it is from 0.1 to 20 weight % of rhodium and from 0.1 to 25 weight % of the promoter(s). Preferred are catalysts containing from 1.0 to 10 weight % of rhodium and from 0.1 to 20 weight % of promoter(s).

For carrying out the process of the invention, gas mixtures consisting completely or substantially of carbon monoxide and hydrogen, optionally containing further components such as nitrogen, argon, carbon dioxide or methane, are passed over the catalysts. The molar ratio of carbon monoxide to hydrogen may be varied within wide limits, preferably in the range of from 5:1 to 1:5, especially 3:1 to 1:3.

The reaction temperatures are generally in the range from 175° to 400° C., preferably 200° to 380° C., and the pressure range 1 to 300, preferably 10 to 200, bar.

It is advantageous to match temperature and pressure in such a manner that a high selectivity to the intended compounds is ensured, and the exothermal formation of methane incited by elevated temperatures is kept low. Therefore, a high pressure and a temperature as low as possible is preferred. The conversion rate of carbon monoxide should generally not exceed 50%, because a higher conversion rate tends to cause increased formation of by-products, among which high molecular weight liquid hydrocarbons and oxygen-containing products may occur in addition to methane, carbon dioxide and gaseous hydrocarbons.

The process is preferably carried out in the gaseous phase, for which the customary solid bed reactors may be used. In order to ensure a good heat dissipation, the thickness of the catalyst layer is advantageously kept low. Alternatively, reactors containing a moving catalyst bed, or fluidized bed reactors are also suitable.

In an especially preferred embodiment of the invention, the reaction is carried out in the gaseous phase in a circulation apparatus where after separation of the condensable reaction products the unreacted gas mixture is recycled to the reactor. This mode of operation is particularly economical allowing elevated reaction temperatures and thus increased space/time yields at unchanged selectivity due to the dilution of the fresh gas with the recycled residual gas containing less hydrogen. As circulation equipment, apparatus with internal or external gas circulation may be used.

The following examples illustrate the invention without limiting it in any way in its scope. By "Nl", there is to be understood liters measured under normal conditions. The percentages are by weight in all cases.

I. General description of the tests

The operations of the Examples are carried out in a tube reactor equipped for pressure reactions, which is heated by a salt bath and consists of a stainless steel tube having an inner diameter of 16 mm and a coaxially mounted thermometer tube having an outer diameter of 6 mm. The reactor is provided with a gas preheater, a cooler for condensation of the reaction products, and a receiver. The reactor is fed with 100 ml each of the catalysts described sub II.

For Examples 1 to 11 and Comparative Examples 1 to 3, 140 Nl/h of a mixture of carbon monoxide and hydrogen in a volume ratio of 1:1 are passed over the catalyst. The reaction pressure is 20 bar and the inner temperature of the reactor is 310° C. The reaction mixture is cooled and the uncondensed portions are depressurized. The composition of condensate and off-gas is determined by gas chromatography For Examples 12 to 16 and Comparative Examples 4 and 5, the same apparatus is used; however, in these cases 400 Nl/h of the mixture of carbon monoxide and hydrogen in a volume ratio of 1:1 are passed over the catalyst at 70 bar and 330° C.

II. Preparation of the catalysts 44 g each of granulated silicic acid having a BET surface of 270 m$^2$/g, a grain size of 1.2 to 3.0 mm, a pore volume of 1.27 ml/g, a bulk density of 0.44 kg/l and a sodium content of 0.4% are impregnated with a solution of the salts listed as follows in 50 ml of water each:

| Comparative Examples | Salt | Salt per 50 ml of water |
|---|---|---|
| 1 and 4 | $MgCl_2.6H_2O$ | 1.16 g |
| 2 and 5 | $LaCl_3$ | 0.25 g |
| Example 1 | $ScCl_3$ | 0.46 g |
| Example 2 | $YCl_3.6H_2O$ | 0.47 g |
| Example 3 | $CeCl_3$ | 0.24 g |
| Example 4 | $PrCl_3.7H_2O$ | 0.36 g |
| Example 5 | $NdCl_3.6H_2O$ | 0.35 g |
| Example 6 | $SmCl_3$ | 0.21 g |
| Examples 7 and 13 | $GdCl_3.6H_2O$ | 0.33 g |
| Example 8 | $TbCl_3$ | 0.23 g |
| Examples 9 and 14 | $DyCl_3$ | 0.23 g |
| Examples 10 and 15 | $HoCl_3$ | 0.23 g |
| Examples 11 and 16 | $YbCl_3.6H_2O$ | 0.31 g |

The impregnated carrier is allowed to stand for 1 hour at room temperature, and then dried in a drying cabinet at a temperature below 80° C.

The carrier so treated is subsequently impregnated with a solution of 3.62 g of $RhCl_3 \times H_2O$ (38.0% Rh) in 50 ml of water, and dried in a drying cabinet at a temperature below 80° C.

Subsequently, the catalyst is reduced in a flow tube made from glass by passing over it 6 Nl/h of hydrogen for 1 hour each under normal pressure and a temperature of 225° C., 250° C. and 275° C., respectively.

The catalyst for Comparative Example 3 is prepared as follows: A solution of 4.5 g of $RhCl_3 \times H_2O$ (38.1% of Rh) in 500 ml of water is added to 170 g of $Ce_2O_3$ (100 ml), compressed to tablets, and subsequently concentrated to dryness in a rotation evaporator under reduced pressure and at about 100° C. The catalyst is reduced in the glass vessel by passing over it 6 Nl/h of hydrogen for 1 hour each under normal pressure and a temperature of 225°, 250° and 275° C., respectively, and subsequently in the ractor by passing over it 10 Nl/h of hydrogen for 15 hours at 350° C.

In the following Table I, the test results obtained at 20 bar and 310° C. are listed, and in Table II the results obtained at 70 bar and 340° C. The values are avarage values of 100 service hours each.

TABLE 1

Each catalyst contains 3.0% Rh and 0.3% of the indicated promoter.
Reaction conditions: Pressure 20 bar, temperature 310° C., space velocity 1400 h$^{-1}$.

| Example | Composition of catalyst | STY[1] g/l.h | Selectivities (mol % CO)[2] | | | | | | |
|---|---|---|---|---|---|---|---|---|---|
| | | | AcOH | AcH | EtOH | ΣC$_2$—O | CH$_4$ | C$_2$-C$_4$ hydrocarbons | other substances |
| Comparative Example 1 | Rh—Mg—SiO$_2$ | 76 | 39.2 | 22.1 | 5.6 | 66.9 | 10.6 | 14.3 | 8.2 |
| Comparative Example 2 | Rh—La—SiO$_2$ | 73 | 34.8 | 28.6 | 11.0 | 74.4 | 11.2 | 8.2 | 6.2 |
| Comparative Example 3 | Rh—Ce$_2$O$_3$[2] | 8 | 7.5 | 6.4 | 12.5 | 26.4 | 30.6 | 15.6 | 27.4 |
| Example 1 | Rh—Sc—SiO$_2$ | 83 | 28.2 | 37.6 | 11.4 | 77.2 | 9.4 | 6.5 | 6.9 |
| Example 2 | Rh—Y—SiO$_2$ | 106 | 22.8 | 44.3 | 8.9 | 76.0 | 9.3 | 7.2 | 7.5 |
| Example 3 | Rh—Ce—SiO$_2$ | 76 | 36.7 | 30.0 | 10.5 | 77.2 | 8.7 | 5.2 | 8.0 |
| Example 4 | Rh—Pr—SiO$_2$ | 75 | 34.0 | 31.6 | 12.5 | 78.1 | 7.6 | 6.2 | 8.1 |
| Example 5 | Rh—Nd—SiO$_2$ | 77 | 31.4 | 32.1 | 11.4 | 74.9 | 9.6 | 7.3 | 8.2 |
| Example 6 | Rh—Sm—SiO$_2$ | 75 | 26.8 | 39.5 | 10.8 | 77.1 | 7.8 | 7.5 | 7.6 |
| Example 7 | Rh—Gd—SiO$_2$ | 88 | 25.8 | 41.9 | 9.3 | 77.0 | 8.8 | 7.3 | 6.9 |
| Example 8 | Rh—Tb—SiO$_2$ | 82 | 26.2 | 42.4 | 9.5 | 78.1 | 7.3 | 7.0 | 7.6 |
| Example 9 | Rh—Dy—SiO$_2$ | 89 | 24.9 | 40.0 | 10.3 | 75.2 | 8.9 | 7.8 | 8.1 |
| Example 10 | Rh—Ho—SiO$_2$ | 90 | 25.2 | 46.9 | 10.2 | 82.3 | 5.8 | 6.2 | 5.7 |
| Example 11 | Rh—Yb—SiO$_2$ | 102 | 25.7 | 46.8 | 7.4 | 79.9 | 6.9 | 7.0 | 6.2 |

[1]STY = space/time yield of oxygen-containing C$_2$ compounds (C$_2$—O = acetic acid, acetaldehyde and ethanol) per l of catalyst and hour
[2]mol % CO relative to reacted carbon monoxide
[3]catalyst in Comparative Example 3 contains 0.95 weight % Rh on Ce$_2$O$_3$.

TABLE 2

Each catalyst contains 3.0% Rh and 0.3% promoter
Reaction conditions: Pressure 70 bar, temperature 330° C., space velocity 4000 h$^{-1}$.

| Example | Composition of catalyst | STY[1] g/l.h | Selectivities (mol % CO)[2] | | | | | | |
|---|---|---|---|---|---|---|---|---|---|
| | | | AcOH | AcH | EtOH | ΣC$_2$—O | CH$_4$ | C$_2$-C$_4$ hydrocarbons | other substances |
| Comparative Example 4 | Rh—Mg—SiO$_2$ | 348 | 45.2 | 20.5 | 6.5 | 72.2 | 13.2 | 10.6 | 4.0 |
| Comparative Example 5 | Rh—La—SiO$_2$ | 364 | 25.9 | 28.5 | 22.4 | 76.8 | 11.5 | 6.0 | 5.7 |
| Example 12 | Rh—Y—SiO$_2$ | 373 | 18.3 | 24.7 | 37.2 | 80.2 | 6.6 | 7.4 | 5.8 |
| Example 13 | Rh—Gd—SiO$_2$ | 392 | 19.8 | 23.5 | 34.8 | 78.1 | 7.8 | 6.9 | 7.2 |
| Example 14 | Rh—Dy—SiO$_2$ | 385 | 18.9 | 34.5 | 27.6 | 81.0 | 6.4 | 5.9 | 6.7 |
| Example 15 | Rh—Ho—SiO$_2$ | 377 | 18.8 | 32.7 | 27.6 | 79.1 | 7.1 | 8.6 | 5.2 |
| Example 16 | Rh—Yb—SiO$_2$ | 443 | 18.5 | 36.7 | 25.3 | 80.5 | 6.9 | 6.2 | 6.4 |

[1], [2]see footnotes of Table 1

What is claimed is:

1. A method for making a mixture containing acetic acid, acetaldehyde, and ethanol as the principal products, which method comprises reacting carbon monoxide and hydrogen at an elevated temperature and an elevated pressure in the presence of a supported catalyst prepared by a method consisting of impregnating a silicic acid or silicate carrier with a catalytic composition consisting essentially of a salt or complex of rhodium and a promotor which is a chloride of at least one element selected from the group consisting of Sc, Y, Ce, Pr, Nd, Sm, Gd, Tb, Dy, Ho, and Yb.

2. A method for making a mixture containing acetic acid, acetaldehyde, and ethanol as the principal products, which method comprises reacting carbon monoxide and hydrogen at an elevated temperature and an elevated pressure in the presence of a supported catalyst prepared by a method consisting of impregnating a silicic acid or silicate carrier with a catalytic composition consisting essentially of a salt or complex of rhodium and a promotor which is a chloride of at least one element selected from the group consisting of Sc, Y, Ce, Pr, Nd, Sm, Gd, Tb, Dy, Ho, and Yb, and then reducing said catalyst.

3. A method for making a mixture containing acetic acid, acetaldehyde, and ethanol as the principal products, which method comprises reacting carbon monoxide and hydrogen at an elevated temperature and an elevated pressure in the presence of a supported catalyst prepared by a method consisting of impregnating a silicic acid or silicate carrier with a catalytic composition consisting essentially of a salt or complex of rhodium, a promoter which is a chloride of at least one element selected from the group consisting of Sc, Y, Ce, Pr, Nd, Sm, Gd, Tb, Dy, Ho, and Yb, and with a cocatalytically active compound which is a compound of Mg, La, Mn, W, Fe, or of an alkali metal.

4. A method for making a mixture containing acetic acid, acetaldehyde, and ethanol as the principal products, which method comprises reacting carbon monoxide and hydrogen at an elevated temperature and an elevated pressure in the presence of a supported catalyst prepared by a method consisting of impregnating a silicic acid or silicate carrier with a catalytic composition consisting essentially of a salt or complex of rhodium, a promoter which is a chloride of at least one element selected from the group consisting of Sc, Y, Ce, Pr, Nd, Sm, Gd, Tb, Dy, Ho, and Yb, and with a cocatalytically active compound which is a compound of Mg, La, Mn, W, Fe, or of an alkali metal, and then reducing said catalyst.

5. A method as in claim 1 wherein said element is Y, Gd, Dy, Ho, or Yb.

6. A method as in claim 2 wherein said element is Y, Gd, Dy, Ho, or Yb.

7. A method as in claim 3 wherein said element is Y, Gd, Dy, Ho, or Yb.

8. A method as in claim 4 wherein said element is Y, Gd, Dy, Ho, or Yb.

* * * * *